Figure 1:
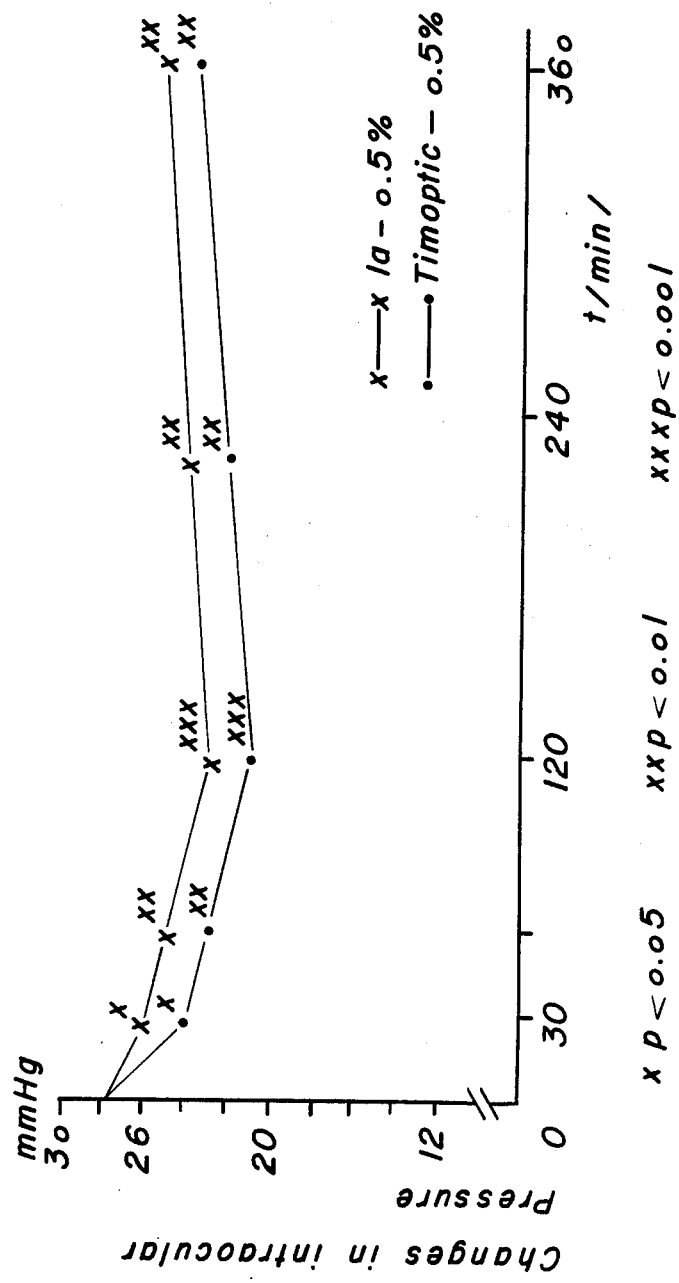

United States Patent [19]

Markov et al.

[11] Patent Number: 4,923,877
[45] Date of Patent: May 8, 1990

[54] COMPOSITION AND METHOD FOR TREATING GLAUCOMA

[75] Inventors: Marko T. Markov; Chavdar B. Ivanov, both of Sofia; Deltcho G. Jelyazkov, Varna; Diana M. Mondeschka, Sofia; Nikolina D. Berova, Sofia; Rositza S. Rakovska, Sofia; Maria G. Todorova, Sofia; Diana D. Popova, Sofia; Emiliya D. Slavova, Sofia; Tatyana S. Zikolova, Sofia; Viola M. Marinova, Sofia; Radi G. Ovcharov, Sofia; Petko D. Uzunov, Sofia; Jossif N. Nissimov, Sofia; Dobrinka G. Gentcheva, Sofia, all of Bulgaria

[73] Assignee: Pharmachim, Sofia, Bulgaria

[21] Appl. No.: 163,595

[22] Filed: Mar. 3, 1988

[51] Int. Cl.$^5$ ............................................. A61K 31/44
[52] U.S. Cl. .................................... 514/284; 514/913
[58] Field of Search ............................. 514/284, 913

[56] References Cited

PUBLICATIONS

Goodman and Gilman's, Seventh Edition, pp. 123-125, (1985).
Berezhinskaya E. E. Aleshinskaya—Pharmacol i toxicol.
Ivanov C. N. Ivanova et al., Inventor's Cert. No. 32353.
Amin A. T. Subbajah—Canada J. Microbio., 15(9), 1969.
Arrata M.—Ocular phar. London Acad., 1980.
Ikram L.—Planta Med., 28(4), 1975, pp. 353-358.
Jamahara J. T. Konoshima—Chem. Pharm. Bull., 1976.
Katz, I.—Invest. Ophthalmol. Vis. Sci., 15, 1976.
Katz, I.—Ann. Phthalmol., 10m, 1978, pp. 847-850.
Kosman, M.—JAMA, 241, 1979, p. 2301-2303.
Leydhecker, W.—Klin. Monatsblaelter fuer Augenheilkunde, 171, 1977.
Schiffer, H.—Merck Sharp Dohme Intern., 1978, pp. 49-52.
Zimmermann, T.—Ophthalmol. Vis. Sci., 16, 1977, pp. 687-688.

*Primary Examiner*—Douglas W. Robinson
*Assistant Examiner*—Zohreh A. Fay
*Attorney, Agent, or Firm*—Klein & Vibber

[57] ABSTRACT

An antiglaucoma composition containing as the active component a s-/-/-2,3 dihydroxy-9,10,11-trimethoxy-5,8,13,13a-tetrahydro-6H-dibenzo (a,f) quinolizine hydrochloride of the general formula:

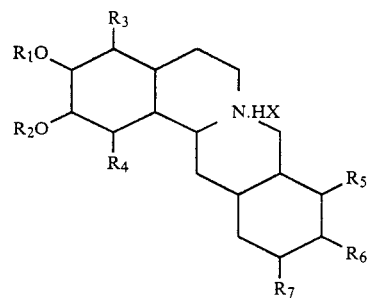

where $R_1=R_2=R_3=R_4=H=R_5=R_6=R_7=CH_3O$

The composition is used as an ophthalmic solution in a method for treating glaucoma by administering a therapeutic dose of 2 to 3 drops two to four times daily to a host such as a warm-blooded animal having glaucoma.

6 Claims, 3 Drawing Sheets

COMPOSITION AND METHOD FOR TREATING GLAUCOMA

BACKGROUND OF THE INVENTION

The invention concerns a composition and a method for treating glaucoma in a host having this condition.

It is known that the most used preparations in the treatment of glaucoma are pylocarpine, epinephrine and timolol. However along with their good therapeutic effect these preparations exhibit many side effects. For example pylocaprine provokes myosis, spasm of muscles around the eye, hyperemia of conjunctivate, and allergic reactions in the eye. (Okeda, A. et al -Duodecim, 95, 1979, p. 11–15, and Schiffer, H. -Merck Sharp Dohme Intern., 1978, p. 49–52) Epinephrine has a slight and momentary effect on the intraocular pressure and provokes tachicardia, midriasis, hyperemia. (Katz, I. -Ann. Phthalmol., 10 m 1978, p. 847–850, and Leydhecker, W. -Klin. Monatsblatt der Augenheilkunde, 171, 1977, p. 538–547) Timolol in local administration causes several side effects including bradicardia, hypotension and bronchospasm, in particular, in the case of persons suffering from asthma and bronchitis, central nervous system depression and sedation. (Arrata, M. -Ocular pharmacology of timolol drops, London Acad. Press 1980; Katz, I. -Invest. Ophthalmol. Vis. Sci., 15, 1976, p. 489–492; Kosman, M. -JAMA, 241, 1979, p. 2301–2303, and Zimmermann, T. -Ophthalmol. Vis. Sci., 16, 1977, p. 687–688) These side effects limit its use in medicine.

OBJECT OF THE INVENTION

An object of this invention is to provide an antiglaucoma composition which does not change significantly the arterial pressure and the chronotropic heart function in normotensive animals and does not exhibit an irritating effect and allergic reaction when it is adminstered locally in the eye.

Another object is to provide a method for treating glaucoma.

These objects are attained by using a physiologically tolerable salts of hexahydrodibenzo (a,f) quinolizines in racemate or optically active forms having the general formula I below:

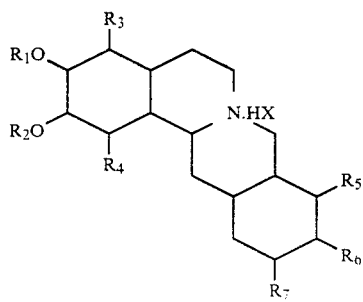

FORMULA I where $R_1$ and $R_2$ are H, $CH_3$, $CH_3CO$; $R_3$ and $R_4$ are H,OH; $R_5$, $R_6$ and $R_7$ are OH, H, $CH_3O$ and X is Cl.

DISCLOSURE OF PREFERRED MODE

It is known that some hexahydrodibenzo (a,f) quinolizines of synthetic or plant origin cause a momentary hypotensive action (Shimamoto, K. -Nippon Iakugaku Zasshi, 53, 1957, p. 75–80) anticholinesterase activity (Berezhinskaja, V., E. Aleshinskaja, -Pharmacol. i toxicol., 31, 1968, p. 1) and a depressive effect on the central nervous system. (Jamahara, J., T. Konoshima -Chem. Pharm. Bull., 24 (8), 1976, p. 1902–1912) Besides some of them manifest biliary antibacterial (Amin, A., T. Subbajah -Can. J. Microbio., 15 (9), 1969, p. 1067–1076) antiinflammatory and antiulceric action. (Ikram, L. -Planta Med., 28 (4), 1975, p. 353–358) However, the antiglaucoma activity of hexadydrodibenzo (a,f) quinolizines was not known previously. The highest antiglaucoma activity in this salt series is manifested by s-/-/-2,3-dihydroxy-9,10,11-trimethoxy-5,8,13,13a-tetrahydro-bH-dibenzo (a,f) quinolizine hydrochloride - Ia, the method of preparation and the physio-chemical properties of which are described in Bulgarian inventor's certificate No. 32353. (Ivanov, C., N. Ivanova et al., Inventor's certificate BG 32353)

The advantages of the compounds with general formula I according to the invention are as follows:

they do not provoke bronchospasm and bradicardia in systematic local administering by comparison with timolol;

they cause only a slightly expressed and momentary hypotensive effect;

they do not irritate the eye when given locally (in the eye);

they do not cause myosis, hyperemia or allergic reactions when locally and systematically given in the eye.

The compounds of general formula I can be used in the treatment of glaucoma in the form of ophthalmologic solutions (collyres) being aqueous solutions of the active component and supplementary pharmaceutical substances. The ophthalmic solutions according to the invention contain from 0.25 to 0.5% of the compound Ia which has exhibited the highest activity. The ophthalmic solutions are sterile and can contain antimicrobial agents such as benzalkonic chloride, phenylmercury, nitrate, timerosal. Thiourea, thioglycerine, ascorbinic acid or sodium metabisulphite can be used as antioxidants. The ophthalmic solutions are prepared by using known methods.

The ophthalmologic solutions according to the invention are administered in therapeutic doses from 2 to 3 drops—two to four times a day. They are particularly effective with warm-blooded animals.

The invention is better illustrated in non-limiting fashion by the following examples:

EXAMPLE 1

To prepare an opthalmologic solution the following are mixed:

| | |
|---|---|
| s-/-/-2,3-dihydroxy-9,10,11-trimetoxy-5,8,13,13a-tetrahydro-6H-dibenzo (a,f) quinolizine hydrochloride (Ia) | 50 g |
| Sodium metabisulphite | 4 g |
| Disodium salt of EDTA | 2 g |
| Benzalkonic chloride | 1 g |
| Glycerine | 470 g |
| Water for injections | up to 10 l |

The freshly distilled water for injections is boiled for 20 to 30 min. and then it is saturated by bubbling in it pure nitrogen and cooled to 40°–50° C. In approximately 8 l of thus saturated water are dissolved consecutively: sodium metabisulphite, disodium salt of EDTA, the compound Ia, glycerine and benzalkonic chloride while continuously saturating with nitrogen. The ready solution is filtered through a Minipore type filter with a 0.22μ membrane. The ampoule filling is performed with double nitrogen gasing.

EXAMPLE 2

Study of Ophthalmotonus

The studies are carried out on the ophthalmotonus of not narcotized and normotensive rabbits. In one series of experiments the introcular pressure was measured by means of the tonometer of Schiotz and it is calculated in mm Hg after the Leydhecker scale while in another series it was measured by means of the tonometer Maklakov. The comparative experiments carried out with compound Ia and timolol administered locally in the eye in the form of 0.5% aqueous solution indicate that compound Ia decreases in a statistically significant manner and with a maximum at the 60 to 120 minutes-the intraocular pressure that is measured by means of the Schiotz tonometer whereby there is no significant difference of its effect compared with that of timolol (see FIG. 1).

Figure 2:
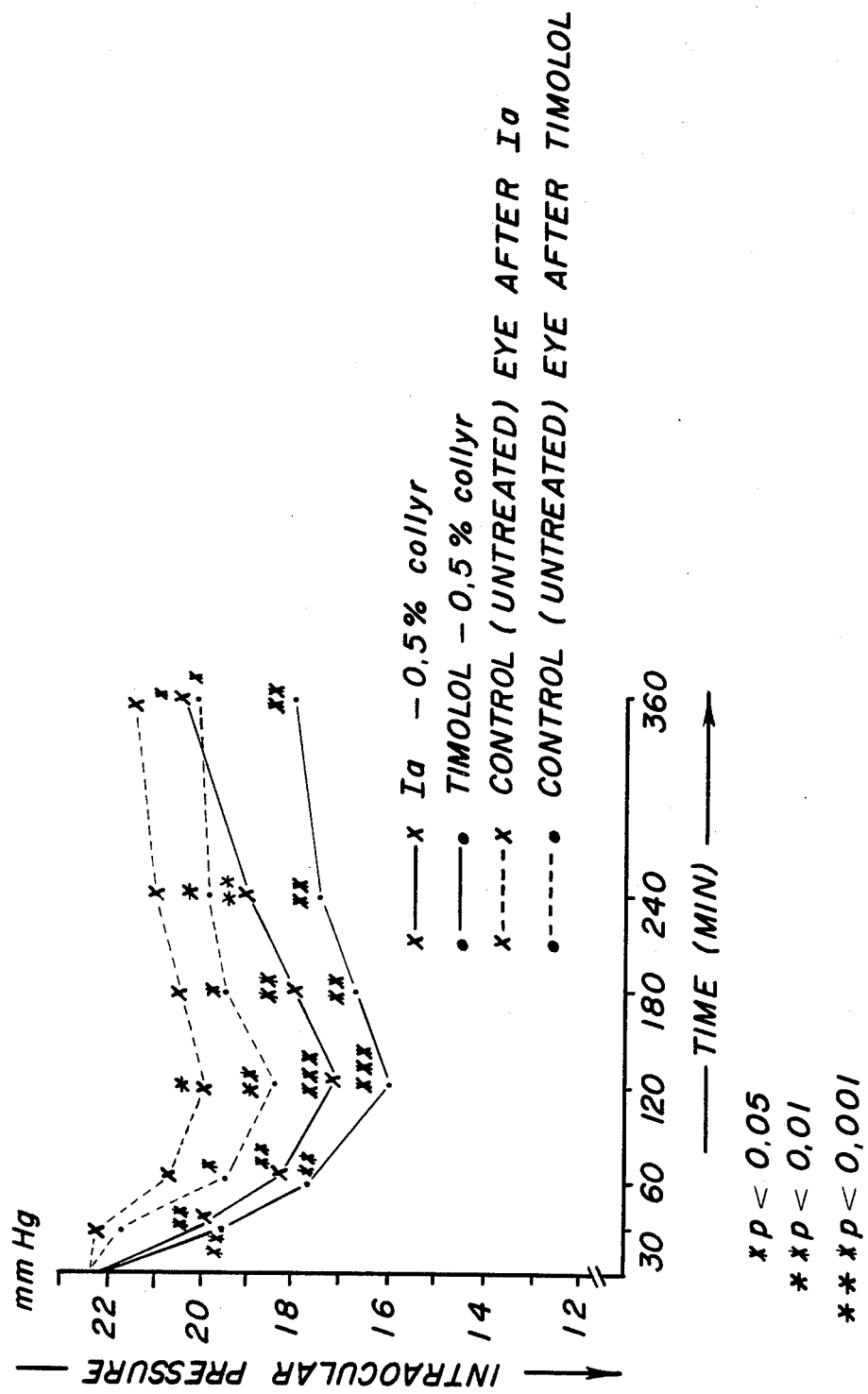

The compound Ia is tested in the form of an ophthalmic solution (collyre)—0.5% aqueous solution. Administered in this therapeutic form it also decreases the intraocular pressure measured by the tonometer of Maklakov (FIG. 2). The comparative tests performed on not narcotized rats of the "Vistar" line show that the compound Ia by contrast to timolol does not cause statistically significant changes in arterial pressure and cardiac frequency (Table 1), when administered locally.

EXAMPLE 3

Influence on the heart-blood vessel system

The compound Ia when administered in doses 0.1 or 0.5 or 1 or 2 or 3 or 5 mg/kg intravenously reduces arterial pressure of narcotized cats and rabbits. Its hypotensive effect in particular in low doses is lightly expressed and momentary. In case of a dose 0.25 mg/kg it is 22% during 10 min (see Table 2):

TABLE 2

Influence of compound Ia on the arterial pressure of cats

| Dose mg/kg | Hypotensive effect % | Duration min. |
|---|---|---|
| 0.1 | 18 | 8 |
| 0.25 | 22 | 10 |
| 0.5 | 25 | 24 |
| 1 | 33 | 30 |
| 2 | 38 | 45 |
| 3 | 42 | over 60 |

TABLE 2-continued

Influence of compound Ia on the arterial pressure of cats

| Dose mg/kg | Hypotensive effect % | Duration min. |
|---|---|---|
| 5 | 52 | over 60 |

The pharmacological analysis with several mediators and other test substances proves that with compound Ia (dose of 3 mg/kg) the effects of dopamine and isoprenaline with respect to arterial pressure are reduced as well as the pressure effect from the occlusion of aa. carotes communis while the pressure effect of nor-adrenaline is increased. This is related probably to the stimulation of presinaptic beta-receptors which facilitates the liberation of the mediator nor-adrenaline (Table 3). The hypotensive effect of compound Ia is considerably suppressed with propranolol—1.5 mg/kg administered intravenously.

Figure 3:
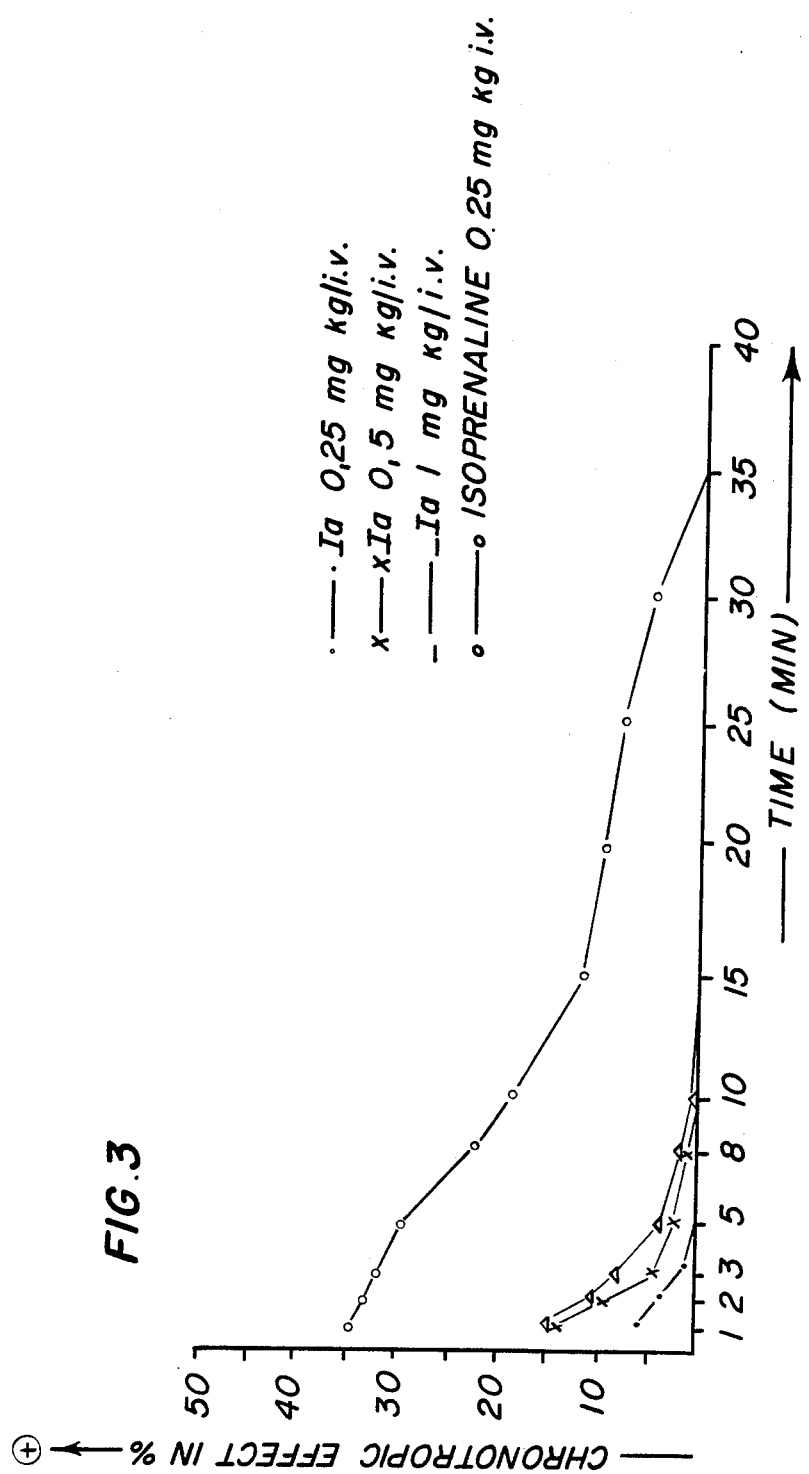

The pharmacological investigations carried out on not narcotized rabbits show that compound Ia exhibits a considerably slighter expressed and a shorter positive chronotropic effect by comparison with isoprenaline while it does not provoke statistically significant changes in the chronotropism of the heart (FIG. 3). By contrast with the timolol the compound Ia does not change in a statistically significant manner the chronotropic function of the heart (FIG. 4).

FIGURE 3

Interaction of compound Ia with some mediators and other test substances with respect to arterial pressure of cats

| Test substances | Ia mg/kg | Changes in arterial pressure, in % | |
|---|---|---|---|
| | | before | after |
| Dopamine-20 μg/kg | 2 | −16.6 | −8.3 |
| Dopamine-40 μg/kg | 2 | −23.0 | −4.2 |
| Isoprenaline-1.5 μg/kg | 3 | −30.5 | −8.8 |
| Noradrenaline-3 μg · kg | 1.5 | +21.0 | +46.0 |
| Noradrenaline-3 μg · kg | 3.0 | +17.0 | +33.0 |
| Histamine-5 μg/kg | 5 | −52.0 | −23.0 |
| Occlusion of aa · carotes communis | 2 | | −40.0 −53.0 |
| Propranolol-1.5 mg/kg | 2 | −42.0 | −24.0 |

TABLE 1

Comperative effects of compound Ia and timolol on arterial pressure and cardiac frequency in local administering on rats of "Wistar" line

| SUB-STANCE | Initial Arterial pressure mm, Hg | | cardiac frequency | 20 min. Arterial pressure mm, Hg | | cardiac frequency | 60 min. Arterial pressure mm, Hg | | cardiac frequency |
|---|---|---|---|---|---|---|---|---|---|
| | systolic | diastolic | | systol. | diastol. | | systol. | diastol. | |
| Ia - 0.5% collyze | 182 ± 21.9 | 144 ± 19.7 | 384 ± 24.2 | 164 ± 18.7 (p > 0.05) ↓9.9% | 124 ± 17.8 (p > 0.05) ↓13.9% | 388 ± 22.2 (p > 0.05) | 131 ± 11.2 (p > 0.05) ↓28% | 96 ± 12.9 (p > 0.05) ↓33.3% | 362 ± 15.3 (p > 0.05) ↓5.7% |
| Timolol - 0.5% collyze | 198 ± 7.3 | 168 ± 7.0 | 405 ± 17.9 | 184 ± 8.4 (p > 0.05) ↓7% | 155 ± 8.0 (p > 0.05) ↓7.7% | 339 ± 20.2* (p < 0.05) ↓16% | 162 ± 8.8* (p < 0.05) ↓18% | 135 ± 9.0* (p < 0.05) ↓20% | 314 ± 9.7** (p < 0.01) ↓22% |

* p < 0.05 |n = 12|
** p < 0.01

EXAMPLE 4

Study of local tolerance

The local tolerance of compound Ia in the form of a collyre (0.5% aqueous solution) was tested by two methods:

(a) Method of Marzuli and Simon, verified and implemented by Marzuli and Ruglas. In this experiment there were tested 12 white rabbits of both sexes with body weight 3200 to 4000 g distributed in two groups of 6 each. The first group was treated with the collyre while the second was treated only with the vehiculum of the collyre. In the conjunctival socket of one eye is applied 0.1 ml of the sample while the other eye serves as control. The local ocular reaction is determined at the first hour, 24th, 48th, 72nd hour and on the 7th day after the treatment. The standard system assumed by the cited authors is applied; namely from 0 to 4 for the cornea, from 0 to 2 for the iris hyperemia. In recording the dynamics of both groups local irritation was not observed and in all three parameters followed up: cornea, iris and conjunctive. The results thus obtained indicate that compound Ia is well-tolerated, its application in the medical practice brings no risk of causing irritative blepharitis, conjunctivitis, toxic damage of cornea or of the entire eye.

(b) Method of Mac Donald, the tests were carried out on 12 white rabbits in an equal number of males and females with an average weight of 3700 g distributed in two groups of six. The first group was treated with the collyre while the second only with its carrier. In the conjunctival socket of one eye is added dropwise 0.05 ml of the studied sample three times a day for 5 days. The local ocular reaction is noted every day prior to the respective treatment of cornea, iris and conjunctive and then it is compared with the control, non-treated, eye of each rabbit. In the case of threefold recording during the five days of treatment changes in the three parameters studied were not observed.

CROSS REFERENCED LITERATURE

Okeda, A. et al—Duodecim, 95, 1979, p. 11–15;
Schiffer, H.—Merck Sharp Dohme Intern., 1978, p. 49–52;
Katz, I.—Ann. Phthalmol., 10 m 1978, p. 847–850;
Leydhecker, W.—Klin. Monatsblatt der Augenheilkunde, 171, 1977, p. 538–547;
Arrata, M.—Ocular pharmacology of timolol drops, London Acad. Press 1980;
Katz, I.—Invest. Ophthalmol. Vis. Sci., 15, 1976, p. 489–492;
Kosman, M.—JAMA, 241, 1979, p. 2301–2303;
Zimmermann, T.—Ophthalmol. Vis. Sci., 16, 1977, p. 687–688;
Shimamoto, K.—Nippon Iakugaku Zasshi, 53, 1957, p. 75–80;
Berezhinskaja, V., E. Aleshinskaja,—Pharmacol. i toxicol., 31, 1968, p. 1;
Jamahara, J., T. Konoshima—Chem. Pharm. Bull., 24 (8), 1976, p. 1902–1912;
Amin, A., T. Subbajah—Can. J. Microbio., 15 (9), 1969, p. 1067–1076;
Ikram, L.—Planta Med., 28 (4), 1975, p. 353–358
Ivanov, C., N. Ivanova et al., Inventor's certificate BG 32353
Velludo et al.—Lucrarile present. Conf. Natl. Farm., Bucharest, 1958, p. 351–354

We claim:

1. An antiglaucoma composition in unit dosage form comprising a carrier and as active component from 0.25%–0.5% of a hexahydrodibenzo (a, f) quinolizine in a collyre in racemic or optically active form of general formula I:

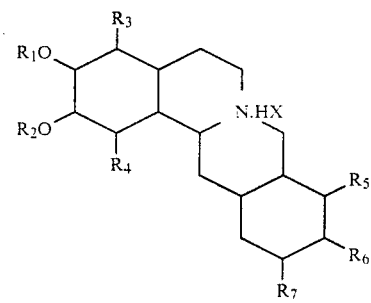

where $r_1$ and $R_2$ are H, $Ch_3$, or $CH_3CO$; $R_3$ and $R_4$ are H or OH; $R_5$, $R_6$ and $R_7$ are H, OH or $CH_3O$; X is a halogen, and pharmaceutically acceptable salts thereof-in an amount effective to treat glaucoma in a host having this condition, said composition being characterized by not irritating the eye or causing myosis, hyperemia or allergic reactions when locally and systematically given in the eye, said composition not causing bronchospasm or brandicardia and only momentary hypotensive effect.

2. An antiglaucoma composition according to claim 1 containing as the active component s-/-/-2, 3-dihydroxy-9,10,11-trimethoxy-5,8,13, 13a-tetrahydro-6H-dibenzo (a,f) quinolizine hydrochloride ($R_1=R_2=R_3=R_4=H$ and $=R_5=R_6=R_7=CH_3O$).

3. An antiglaucoma composition according to claim 1, in the form of a 0.5% ophthalmic solution.

4. A method of treating glaucoma which comprises administering locally in the eye a therapeutic amount of the composition of claim 1.

5. The method of claim 4, comprising administering an effective amount of the composition of claim 2.

6. The method of claim 4, comprising administering said solution at a strength of 0.25 to 0.5%.

* * * * *